(12) United States Patent
Bjork et al.

(10) Patent No.: US 6,518,312 B2
(45) Date of Patent: Feb. 11, 2003

(54) IMMUNE ENHANCEMENT

(75) Inventors: Anders Bjork, Bjaerred (SE); Gunnar Hedlund, Lund (SE); Tomas Leanderson, Malmoe (SE)

(73) Assignee: Active Biotech AB, Lund (SE)

( * ) Notice: Subject to any disclaimer, the term of this patent is extended or adjusted under 35 U.S.C. 154(b) by 0 days.

(21) Appl. No.: 09/897,023

(22) Filed: Jul. 3, 2001

(65) Prior Publication Data

US 2002/0019385 A1 Feb. 14, 2002

Related U.S. Application Data

(60) Provisional application No. 60/216,329, filed on Jul. 5, 2000.

(51) Int. Cl.$^7$ .............................................. A61K 31/165
(52) U.S. Cl. ........................ 514/619; 514/617; 564/157; 564/192; 548/215; 548/556
(58) Field of Search ................................ 514/613, 617, 514/619, 621; 564/152, 155, 157; 546/186, 192; 548/215, 300.1, 556

(56) References Cited

U.S. PATENT DOCUMENTS 6,211,239 B1 * 4/2001 Fontana ...................... 514/569

OTHER PUBLICATIONS

CA: 129:156613 abs of Carcinogenesis by Ohata et al 19 (6) pp. 1007–1012 1998.*
CA:119:203167 abs of CA 2073833 Mar. 1993.*
CA:126:126885 abs of WO 964664 Dec. 1996.*
CA:128:213397 abs of JP10036272 Feb. 1998.*
CA:109:22628 abs of J Med Chem by Robertson et al 31 (7) pp. 1290–5 1988.*
CA:129:184175 abs of Mol Brain Res by Yuan et al 58(1,2) pp 225–230 1998.*

CHEMCATS accession No. 2001:126051 chemical library TimTec Inc Feb. 2001.*

(List continued on next page.)

Primary Examiner—Jean F. Vollano
(74) Attorney, Agent, or Firm—Browdy and Neimark, P.L.L.C.

(57) ABSTRACT

A method for stimulation of transcription factor AP (activator protein)-1 by administering a compound of the formula (I)

(I)

wherein

R is selected from methyl, ethyl, n-propyl, iso-propyl, c-propyl, n-butyl, sec.-butyl, iso-butyl, tert.-butyl, c-butyl, n-pentyl, sec.-pentyl, iso-pentyl, tert.-pentyl, neo-pentyl, c-pentyl, c-hexyl and c-heptyl; $R_{Na}$ and $R_{Nb}$ are the same or different and selected from hydrogen, methyl and ethyl; $R_2$, $R_3$, $R_5$ and $R_6$ are independently selected from hydrogen, methyl, methoxy, thiomethyl, hydroxy, fluoro, chloro, bromo, trifluoromethyl, phenyl and benzyl;

n is 1, 2 or 3;

R' and R" are the same or different and selected from methyl, ethyl, n-propyl, iso-propyl, n-butyl, sec.-butyl, and iso-butyl or R' and R" together form a saturated heterocyclic ring of 5–7 atoms; and pharmaceutically acceptable salts, hydrates and solvates thereof, to a mammal in need thereof.

14 Claims, 1 Drawing Sheet

OTHER PUBLICATIONS

A. Sundstedt et al., "In Vivo Anergized CD4$^+$T Cells Have Defensive Expression and Function of the Activating Protein–1 Transcription Factor", *J Immunol,* Dec. 1998, p. 5930–5936, vol. 161(11).

E. Parra et al., "Costimulation by B7–1 and LFA–3 Targets Distinct Nuclear Factors That Bind to the Interleukin–2 Promoter: B7–1 Negatively Regulates LFA–3–Induced NF–AT DNA Binding", *Mol Cell Biol,* Mar. 1997, p. 1314–23, vol. 17(3).

Pei–Xong Yuan et al., "Lithium Stimulates Gene Expression Through the AP–1 Transcription Factor Pathway", *Mol Brain Res,* Jul. 1998, p. 225–230, vol. 58(1–2).

T.L. Whiteside, "Signaling Defects in T Lymphocytes of Patients with Malignancy", *Cancer Immunol Immunother,* Oct. 1999, p. 346–352, vol. 48(7).

R. Kiessling et al., "Tumor–Induced Immune Dysfunction", *Cancer Immunol Immunother,* Oct. 1999, p. 353–362, vol. 48(7).

R.S. Johnson et al., "Pleiotropic Effects of a Null Mutation in the c–fos Proto–Oncogene", *Cell,* Nov. 1992, p. 577–586, vol. 71(4).

G. Chen et al., "Valproate Robustly Enhances AP–1 Mediated Gene Expression", *Mol. Brain. Res.,* Jan. 1992, p. 52–58, vol. 64(1).

H. Belfrage et al., "Prevention of Superantigen–Induced Tolerance in Vivo By Interleukin–2 Treatment", *Cancer Immunol Immunother,* Apr. 1997, p. 77–82, vol. 44(2).

H. Belfrage et al., "Prevention of Superantigen–Induced Down–Regulation of T–Cell Mediated Cytotoxic Activity By Il–2 in vivo", *Immunology,* Feb. 1997, p. 183–188, vol. 90(2).

Hans Belfrage et al., "Enhanced and Prolonged Efficacy of Superantigen–Induced Cytotoxic T Lymphocyte Activity by Interleukin–2 In Vivo", *Cancer Immunol Immunother,* Aug. 1995, p. 87–94, vol. 41.

\* cited by examiner

IMMUNE ENHANCEMENT

CROSS REFERENCE TO RELATED APPLICATION

This application claims the benefit of U.S. provisional application No. 60/216,329 filed Jul. 5, 2000.

FIELD OF THE INVENTION

The present invention relates to substituted benzamides, which are enhancers of transcription factor AP (activator protein)-1, to compositions containing them, and to methods for clinical treatment of diseases associated with immune suppressive states and to the use of the benzamides for the preparation of a medicament for stimulation of transcription factor AP-1. Such compounds are particularly useful in the treatment of a variety of diseases associated with immune suppression and low capability to produce IL (interleukin)-2. Such diseases include cancer, autoimmune disease and infectious disease. More particularly, the present invention relates to benzamide derivatives suitable for the treatment of, for example, solid tumours, rheumatoid arthritis (RA) and AIDS. The compounds of the present invention are also suitable for the treatment of manic-depressive illness.

BACKGROUND OF THE INVENTION

AP-1 is a transcriptionally active protein heterodimer containing members of the Fos (e.g. c-Fos, FosB, Fra-1, Fra-2) and the Jun (e.g. c-Jun, JunB, JunD) family of proteins. The AP-1 transcription factors are stimulated by e.g. growth factors, cytokines, T cell activators and neurotransmitters and act as dimers binding to DNA in many promoters including proteases and cytokines like IL-2. C-Jun and c-Fos knock-out mice have been produced showing embryonic lethality and osteopetrosis/lymphopenia/behavioural abnormalities, respectively (Johnson et al., 1992). These results emphasise that the AP-1 site is pivotal in many different genes and points out lymphocyte regulation and behaviour, regulation in the central nervous system, as two distinct biological hotspots. Therefore, immune suppression with low capability to produce IL-2 and behavioural disorders are two very different medical indication areas where AP-1 activity is suboptimal and where AP-1 enhancers can be applied.

In U.S. Pat. No. 3,177,252 some substituted benzamide derivatives including metoclopramide (The Merck Index $12^{th}$ Ed., entry 6226) are disclosed as being useful for the treatment of emesis.

The compound metoclopramide may be associated with depression and, because of its central as well as peripheral dopamine-blocking properties, may cause most unwanted tardive dyskinesia. Structure-activity relationship studies have demonstrated the link between the diaminoethylene bridge and the dopamine-$D_2$ blockade.

In GB 1,174,956 quaternary ammonium salts of N-substituted benzamide derivatives and their action to accelerate the automatic motility of digestive tract are disclosed.

In J. Org. Chem. USSR 22, 578–582 (1986), the synthesis of N-(3-dimethylamino-propyl)-3-nitro-4-acetylaminobenzamide is described.

In U.S. Pat. No. 4,568,685 some N-[(1H-1,2,4-triazol-1-yl)alkyl]arylamides are disclosed as being inhibitors of thromboxane synthetase enzyme.

In U.S. Pat. No. 4,568,687 some N-[ω(1H-imidazole-1-yl)alkyl]arylamides are disclosed as being inhibitors of thromboxane synthetase enzyme and are also useful in the treatment of hypertension and myocardial ischemia.

In Analytical Profiles of Drug Substances vol. 4, K Florey, Ed. (Academic Press, New York, 1975) pp 333–383, procainamide (The Merck Index $12^{th}$ Ed., entry 7936) is described as an antiarrhytmic agent.

We have now discovered a novel method of stimulating the transcription factor AP-1 using substituted benzamides.

SUMMARY OF THE INVENTION

Immune Suppression in Cancer, Autoimmune Disease and Infectious Disease

Immune system-based approaches for the treatment of malignant disease have focused on cytolytic effector cells such as cytotoxic T lymphocytes (CTL), and natural killer (NK) cells. It has also been demonstrated that tumour-bearing mice can be cured using a wide variety of approaches, some of which involve IL-2 mediated enhancement of CTL and NK cell activity. However, the apparent success in mice stands in contrast to the current situation in the clinic, wherein only a minority of patients have thus far benefited from CTL- or NK cell-based anti-tumour approaches. This is probably a result from tumour-induced immune suppression (Whiteside, 1999; Kiessling et al., 1999). One of the underlying causes of tumour-associated immune suppression of CTL and NK cell activity, the intracellular signalling deficiency resulting from reduction of the TCR/CD3 zeta chain expression of the T cells, is also shared with HIV infection, leprosy, and rheumatoid arthritis. This signalling deficiency is overrun by IL-2 treatment in vitro. IL-2 is a central cytokine in the development of functional immune responses and it has been clearly shown that the AP-1 site of the IL-2 promoter is pivotal for optimal activity (Sundstedt and Dohlsten, 1998). Distinct benzamides would therefore represent an alternative treatment for immune stimulation and IL-2 enhancement in immune suppressive states of disease. In addition, several treatment regiments such as cytostatic and radiation therapy applied in the treatment of cancer result in unwanted immune suppression, an induced state that would be compensated for by administering compounds of the present invention.

Manic-Depressive Illness

Lithium and sodium valproate (VPA) (The Merck Index $12^{th}$ Ed., entry 10049) are effective in the treatment of bipolar disorders (manic-depressive illness) and may function through the regulation of signal transduction pathways and transcription factors such as c-Fos and c-Jun, which in turn results to changes in gene expression. The long-term efficacy of lithium and VPA in bipolar disorders suggests that the regulation of gene expression may be an important target for these drugs. These two structurally highly dissimilar agents, lithium and VPA, increase AP-1 DNA binding activity in areas of rodent brain ex vivo and in human neuronal cells in culture (Yuan et al., 1998; Chen et al., 1999). Both treatments also increase the expression of a reporter gene driven by an AP-1-containing promoter, and mutations in the AP-1 sites of the reporter gene promoter markedly attenuate these effects. Both treatments also increase the expression of several endogenous proteins, which genes are known to be regulated by AP-1. These effects suggest that the temporal regulation of AP-1 mediated gene expression in critical neuronal circuits may play a role in the long-term therapeutic efficacy of lithium and VPA and point out that also other AP-1 enhancers like distinct benzamides could potentially act as modulators of e.g. manic-depressive illness.

DESCRIPTION OF THE INVENTION

Figure 1:
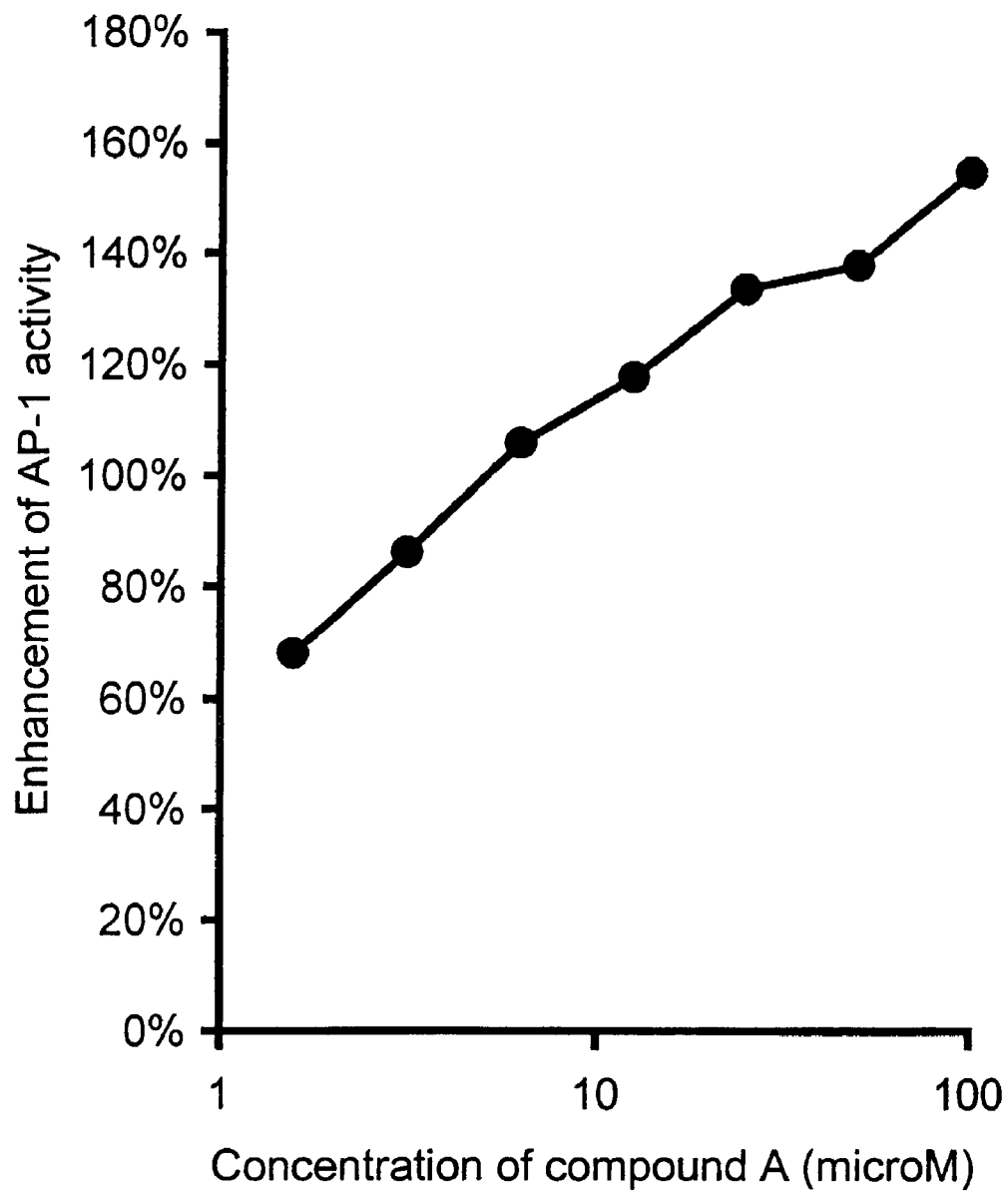
FIG. 1 discloses the percentage enhancement of the reporter gene activity in the assay utilizing Jurkat cells with a transfected AP-1-driven luciferase gene reporter.

A primary objective of the present invention is to provide benzamide compounds which by virtue of their pharmacological profile, with high potency in experimental models and low level of side-effects, are considered to be of value in the treatment of disease associated with immune suppressive states e.g. for the stimulation, enhancement or modulation of the immune response. Included in the invention is also the use of the compounds for the stimulation of transcription factor AP-1. In a particular aspect, this invention provides preparation of a medicament for the stimulation of transcription factor AP-1, a method of treating diseases in which the disease pathology may be therapeutically modified by stimulating AP-1. Examples of such diseases are cancer, autoimmune disease and infectious disease. More particularly, the present invention relates to benzamide derivatives suitable for the treatment of, for example, solid tumours, rheumatoid arthritis (RA) and AIDS. The compounds of the present invention are also suitable for the treatment of manic-depressive illness.

The term "treatment" as used herein includes relieving the symptoms of disease.

It has now surprisingly been found that the compounds of formula (I)

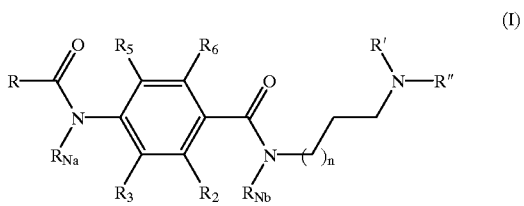

wherein
R is selected from methyl, ethyl, n-propyl, iso-propyl, c-propyl, n-butyl, sec.-butyl, iso-butyl, tert.-butyl, c-butyl, n-pentyl, sec.-pentyl, iso-pentyl, tert.-pentyl, neo-pentyl, c-pentyl, c-hexyl and c-heptyl;

$R_{Na}$ and $R_{Nb}$ are the same or different and selected from hydrogen, methyl and ethyl;

$R_2$, $R_3$, $R_5$ and $R_6$ are independently selected from hydrogen, methyl, methoxy, thiomethyl, hydroxy, fluoro, chloro, bromo, trifluoromethyl, phenyl and benzyl;

n is 1, 2 or 3;

R' and R" are the same or different and selected from methyl, ethyl, n-propyl, iso-propyl, n-butyl, sec.-butyl, and iso-butyl or R' and R" together form a saturated heterocyclic ring of 5–7 atoms having the formula

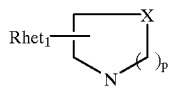

wherein p is 1, 2, 3;
X is selected from $CHRhet_1$, $NRhet_1$ and O with the proviso that p is 2 or 3 when X is $NRhet_1$, and O;
$Rhet_1$ is selected from hydrogen and $C_{1-5}$ alkyl, optionally functionalised with OH, halogen (F, Cl and Br), CN, $COORhet_2$, $N(Rhet_2)_2$ wherein $Rhet_2$ independently is selected from H, $C_{1-4}$ alkyl;
with the proviso that when R' and R" are methyl then R cannot be methyl; and pharmaceutically acceptable salts, hydrates and solvates thereof; are unexpectedly effective and specific in the treatment of individuals suffering from cancer, autoimmune disease, infectious disease and manic-depressive illness.

In a preferred embodiment of the invention

R is selected from methyl, ethyl, n-propyl and iso-propyl, $R_{Na}$ and $R_{Nb}$ are hydrogen, one of $R_2$, $R_3$, $R_5$ and $R_6$ is selected from methyl, methoxy, thiomethyl, hydroxy, fluoro, chloro, trifluoromethyl and phenyl, R' and R" are selected from methyl, ethyl, n-propyl and n-butyl with the proviso that when R' and R" are methyl then R cannot be methyl;.

The compounds of formula (I) were assayed for AP-1 enhancement. The compounds of this invention were tested in assays for the modulation of stimulated activity of an AP-1-driven reporter gene in the Jurkat T cell line. The activation of this reporter gene results in luciferase production and the amounts of produced luciferase parallels the level of AP-1 activity. A high level of AP-1 activity is pivotal to e.g. high production of IL-2.

All embodiments of the invention as disclosed in the claims are herewith included in the specification.

The following examples are intended to illustrate the invention without restricting the scope thereof.

The compounds of formula (I) may be prepared by methods well known in the literature. The general solution preparation is shown in Scheme 1 and 2.

Scheme 1

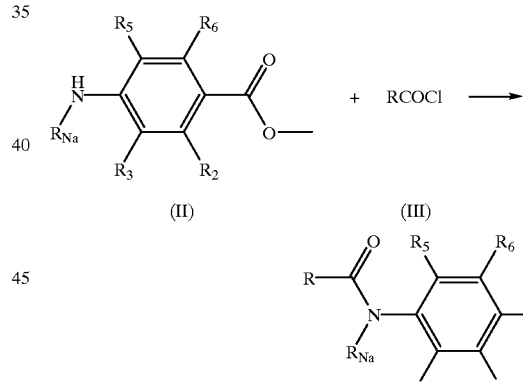

Scheme 2

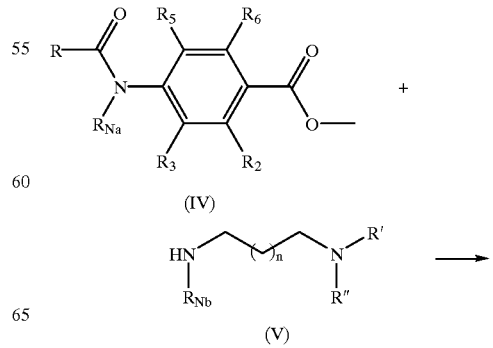

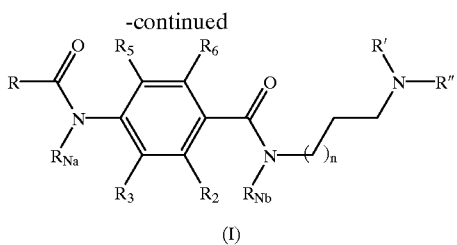

(I)

A benzamide derivative of formula (I) may be prepared by conventional methods and, for example, by first the reaction of a 4-amino-benzoic acid methyl ester (II) with an acid chloride (III) or anhydride in an inert solvent such as dichloromethane in the presence of triethylamine (Scheme 1). The resulting 4-acylamino-benzoic acid methyl esters (IV) and a N,N-substituted alkylenediamine (V) is then condensed in an excess of V in the presence of a catalytic amount ammonium chloride to form the compounds of formula (I) (Scheme 2). Alternatively, the methylester is first hydrolysed and then activated using conventional methods, such as ethylchloroformate, dicyclohexylcarbodiimide (DCC) or 2-(1H-benzotriazol-1-yl)-1,1,3,3-tetramethyluronium tetrafluoroborat (TBTU). The starting materials used herein are commercially available or are prepared by conventional methods found in standard reference books such as the Compendium of Organic Synthetic Methods, vol. I-VI (Wiley-Interscience), well known to those of ordinary skill in the art.

Acid addition salts of the compounds of formula (I) are prepared in a standard manner in a suitable solvent and in excess of an acid, such as hydrochloric, hydrobromic, sulphuric, maleic and succinic acid.

EXAMPLE 1

4-iso-Butyrylamino-2-methoxy-benzoic acid methyl ester 1.81 g of 4-amino-2-methoxy-benzoic acid methyl ester and 1.4 g of triethylamine were dissolved in 20 ml of dichloromethane. 1.23 g of isobutyryl chloride in 5 ml of dichloromethane was added dropwise at 0° C. The reaction mixture was allowed to reach room temperature and stirred for 3 hours. The reaction mixture was washed with water, dried and the solvents were evaporated to yield 1.9 g of the title product.

1H NMR (CDCl$_3$): δ1.22 (6H, d), 2.53 (1H, m), 3.83 (3H, s), 3.83 (3H, s), 6.85 (1H, d), 7.70 (1H, s), 7.75 (1H, d), 7.84 (1H, s).

EXAMPLE 2

N-[(2-Diethylamino)propyl]-4-isobutyrylamino-2-methoxy-benzamide 0.3 g of 4-iso-butyrylamino-2-methoxy-benzoic acid methyl ester was dissolved in 3 ml of N,N-diethyl-propylenediamine together with a catalytic amount of ammonium chloride. The reaction mixture was refluxed for 3 hours. Dichloromethane was added and washing 4 times with water removed excess diamine. Drying and evaporation of the solvents yielded 0.15 g of the title compound.

1H NMR (CDCl$_3$): δ0.97 (6H, t), 1.20 (6H, d), 1.71 (2H, m), 2.48 (6H, m), 2.59 (1H, m), 2.46 (2H, q), 3.90 (3H, s), 6.80 (1H, d), 7.94 (1H, s), 8.03 (1H, d), 8.29 (1H, s).

EXAMPLE 3

N-[3-(Diethylamino)propyl]-4-iso-buturylamino-3-hydroxy-benzamide 4-iso-Butyrylamino-3-hydroxy-benzoic acid (0.089 g) and TBTU (0.128 g) in chloroform (15 ml) was stirred for 2 hours. N,N-Diethyl-propylenediamine (0.052 g) was added and the mixture was stirred for 1 hour. Evaporation of the solvent gave a residue, which was chromatographed on a silica gel column first eluted/washed with ethylacetate and then eluted with ethylacetate-methanol-triethylamine (12:4:1) to yield 0.03 g, of the title product.

1H NMR (CDCl$_3$): δ1.14 (t, 6H) 1.25 (m, 6H) 2.01 (m, 2H) 2.61 (m, 1H) 2.98 (m, 2H) 3.04 (m, 2H) 3.44 (m, 2H) 7.35 (m, 1H) 7.80 (d, 1H) 7.92 (m, 1H) 8.21 (d, 1H) 8.36 (s, 1H).

EXAMPLE 4

4-(N-iso-Butyryl-N-methylamino)-benzoic acid

4-Methylamino-benzoic acid methyl ester (0.41 g) were suspended in chloroform (20 ml). Isobutyryl chloride (0.79 g) in chloroform (10 ml) was added dropwise for 30 minutes and then dropwise triethylamine (1 ml) dissolved in chloroform (5 ml). The reaction mixture was stirred for 3 hours and the solvent was evaporated. 1M NaOH(aq) (40 ml) was added and the mixture stirred overnight. The solution was filtered to remove unsolved material and then acidified with 2M HCl(aq). Filtration and drying in vacuum yielded 0.48 g of the title product.

EXAMPLE 5

N-[3-(Diethylamino)propyl]-4-(N-iso-butyryl-N-methylamino)-benzamide

To a stirred solution of 4-(iso-butyryl-N-methylamino)-benzoic acid (0.088 g) and triethylamine (0.041 g) in chloroform (4 ml) was added a solution of ethyl chlorformate (0.049 g) in chloroform (1 ml). The mixture was stirred under an N$_2$ atmosphere at room temperature for 1½ hours and then cooled to 0° C. N,N-Diethyl-propylenediamine (0.051 g) in chloroform (1 ml) was added and the mixture was stirred over night. The mixture were washed with 0.5 M NaOH(aq) and water. Drying and evaporation of the solvent gave a residue, which was chromatographed on a silica gel column first eluted/washed with ethylacetate and then eluted with ethylacetate-methanol-triethylamine (12:4:1) to yield 0.098 g, of the title product.

1H NMR (CDCl$_3$): δ1.01 (t, 6H) 1.04 (t, 6H) 1.77 (m, 2H) 2.48 (m, 1H) 2.61 (m, 6H) 3.23 (s, 3H) 3.57 (m, 2H) 7.21 (m, 1H) 7.83 (m, 1H) 8.80 (s, 1H).

Examples 6 to 12 were prepared by the method described in Example 5.

EXAMPLE 6

N-[3-(Diethylamino)propyl]-4-iso-butyrylamino-3-methoxy-benzamide

1NMR (CDCl$_3$): δ1.07 (t, 6H) 1.25 (d, 6H) 1.80 (m, 2H) 2.55 (m, 1H) 2.64 (m, 6H) 3.56 (m, 2H) 3.94 (s, 3H) 7.27 (m, 1H) 7.55 (d, 1H) 7.91 (s, 1H) 8.43 (d, 1H) 8.70 (s, 1H).

EXAMPLE 7

N-[3-(Diethylamino)propyl]-4-(iso-butyryl-N-methylamino)-2-methoxy-benzamide

1H NMR (CDCl$_3$): δ1.04 (m, 12H) 1.80 (m, 2H) 2.56 (m, 7H) 3.24 (s, 3H) 6.75 (s, 1H) 6.88 (m, 1H) 7.99 (m, 1H) 8.17 (d, 1H).

EXAMPLE 8

N-(3-morpholinopropyl)-4-iso-butyrylamino-2-methoxy-benzamide

1H NMR (CDCl$_3$): δ1.24 (d, 6H) 1.86 (m, 2H) 2.52 (m, 7H) 3.51 (m, 2H) 3.75 (m, 4H) 3.97 (s, 3H) 6.71 (m, 1H) 7.37 (s, 1H) 7.94 (s, 1H) 8.09 (d, 1H).

EXAMPLE 9

N-[4-(Dimethylamino)butyl]-4-iso-butyrylamino-2-methoxy-benzamide

1H NMR (CDCl$_3$): δ1.25 (d, 6H) 1.65 (m, 4H) 2.37 (m, 6H) 2.52 (m, 3H) 3.45 (m, 2H) 3.97 (s, 3H) 6.73 (m, 1H) 7.43 (s, 1H) 7.88 (m, 1H) 7.92 (s, 1H) 8.09 (d, 1H).

EXAMPLE 10

N-[3-(4-methylpiperazino)-propyl]-4-iso-butyrylamino-2-methoxy-benzamide

1H NMR (CDCl$_3$): δ1.25 (d, 6H) 1.83 (m, 3H) 2.35 (s, 3H) 2.52 (m, 3H) 2.60 (m, 7H) 3.49 (m, 2H) 3.96 (s, 3H) 6.71 (m, 1H) 7.37 (s, 1H) 7.94 (m, 2H) 8.08 (d, 1H).

EXAMPLE 11

N-[3-(Diethylamino)propyl]-4-iso-butyrylamino-3,5-dichloro-benzamide

1H NMR (CDCl$_3$): δ1.10 (t, 6H) 1.29 (d, 6H) 1.82 (m, 2H) 2.69 (m, 7H) 3.55 (m, 2H) 7.03 (s, 1H) 7.82 (s, 2H) 9.22 (s, 1H).

Pharmacological Methods

Cells from the Jurkat T cell line were transfected with an AP-1-driven luciferase gene reporter construct (Parra et al., 1997) together with a selection gene vector. Selected clones from the resulting stable AP-1 reporter gene transfectants were used in the assays for AP-1 transcription factor activity. These transfected Jurkat cells (Jurkat/AP-1rep) were grown in RPMI 1640 supplemented with glutamine, hepes, sodium pyruvate, gentamicin, 10% FCS and G418. To evaluate distinct compounds for their capacity to enhance the AP-1 activity, Jurkat/AP-1rep cells were stimulated for 5.5 h in the temperature of 37° C. with phorbol myristate acetate and ionomycin in the absence and presence of test compounds. The 96 well plates containing the cell cultures were then put on ice until harvested. The supernatants were removed and the cells were lysed. AP-1 activity was measured as luminiscence produced by luciferase substrate, which was added to the wells in conjunction with measurement.

Superantigen responsive mice were treated with Staphylococcal enterotoxin A in accordance with Belfrage et al. (Belfrage et al. 1995, 1997a, 1997b). Plasma and splenocytes were collected at different time points to evaluate the induced activity of T cells with and without treatment with the compounds of formula (I). It is shown that T cell activity as measured as IL-2 production, cytotoxic T cell activity and anergy induction (Belfrage et al. 1995, 1997a, 1997b) were modulated by the treatment.

Among preferred compounds is N-[(2-diethylamino)propyl]-4-isobutyrylamino-2-methoxybenzamide, hereinafter called Compound A. Compound A was shown to enhance the activity of the AP-1 driven reporter in a dose dependent fashion down to μM concentrations (FIG. 1).

The compounds of formula (I) are useful as enhancers of AP-1. The present invention provides useful compositions and formulations of said compounds including pharmaceutical compositions and formulations of said compounds.

Effective quantities of the compounds of formula (I) are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g. solutions, suspensions, emulsions, tablets, capsules, and powders prepared for oral administration, aerosols for inhalations, sterile solutions for parental administration, suppositories for rectal administration or suitable topical formulations. Conventional procedures for the selection and preparation of suitable pharmaceutical formulations are described, for example, in "Pharmaceuticals-The Science of Dosage Form Design", M. B. Aulton, Churchill Livingstone, 1988.

A suitable daily dose for use in the treatment of disease with associated immune suppression or manic-depressive illness is contemplated to vary between 0.0005 mg/kg to about 10 mg/kg body weight, in particular between 0.005 mg/kg to 1 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

Various additives to enhance the stability or ease of administration of the drug are contemplated. The pharmaceutical composition may also contain additional therapeutically useful substances other than a compound of formula (I).

The ability of the compounds of the present invention to enhance the AP-1 activity is clearly evidenced by their ability to enhance the reporter gene activity (see FIG. 1). No unacceptable toxicological effects are expected such as tardive dyskinesia when compounds of the present invention are administered in accordance with the present invention.

References

Belfrage H, Dohlsten M, Hedlund G, Kalland T. 1995 Enhanced and prolonged efficacy of superantigen-induced cytotoxic T lymphocyte activity by interleukin-2 in vivo. Cancer Immunol Immunother 1995 August; 41(2):87–94

Belfrage H, Dohlsten M, Hedlund G, Kalland T. 1997a Prevention of superantigen-induced down-regulation of T-cell mediated cytotoxic activity by IL-2 in vivo. Immunology 1997 February; 90(2): 183–8

Belfrage H, Dohlsten M, Hedlund G, Kalland T. 1997b Prevention of superantigen-induced tolerance in vivo by interleukin-2 treatment. Cancer Immunol Immunother 1997 April; 44(2): 77–82

Chen G, Yuan P X, Jiang Y M, Huang L D, Manji H K. Valproate robustly enhances AP-1 mediated gene expression. Brain Res Mol Brain Res 1999 January 22; 64(1):52–8

Johnson R S, Spiegelman B M, Papaioannou V. Pleiotropic effects of a null mutation in the c-fos proto-oncogene. Cell 1992 November 13;71(4):577–86

Kiessling R, Wasserman K, Horiguchi S, Kono K, Sjoberg J, Pisa P, Petersson M. Tumor-induced immune dysfunction. Cancer Immunol Immunother 1999 October; 48(7):353–62

Parra E, Varga M, Hedlund G, Kalland T, Dohlsten M. Costimulation by B7-1 and LFA-3 targets distinct nuclear factors that bind to the interleukin-2 promoter: B7-1 negatively regulates LFA-3-induced NF-AT DNA binding. Mol Cell Biol 1997 March; 17(3): 1314–23

Sundstedt A, Dohlsten M. In vivo anergized CD4+ T cells have defective expression and function of the activating protein-1 transcription factor. J Immunol Dec. 1, 1998;161(11): 5930–6

Whiteside T L. Signaling defects in T lymphocytes of patients with malignancy. Cancer Immunol immunother 1999 October; 48(7):346–52

Yuan P X, Chen G, Huang L D, Manji H K. Lithium stimulates gene expression through the AP-1 transcription

We claim:

1. A method for stimulation of transcription factor AP-1 (activator protein-1) comprising administering a compound of the formula (I)

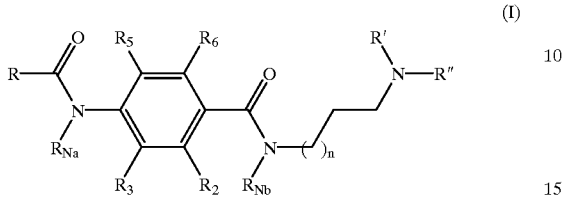

wherein

R is selected from the group consisting of methyl, ethyl, n-propyl, iso-propyl, c-propyl, n-butyl, sec-butyl, iso-butyl, tert-butyl, c-butyl, n-pentyl, sec-pentyl, iso-pentyl, tert-pentyl, neo-pentyl, c-pentyl, c-hexyl and c-heptyl;

$R_{Na}$ and $R_{Nb}$ are the same or different and selected from the group consisting of hydrogen, methyl and ethyl;

$R_2$, $R_3$, $R_5$ and $R_6$ are independently selected from the group consisting of hydrogen, methyl, methoxy, thiomethyl, hydroxy, fluoro, chloro, bromo, trifluoromethyl, phenyl and benzyl;

n is 1, 2 or 3;

R' and R" are the same or different and selected from the group consisting of methyl, ethyl, n-propyl, iso-propyl, n-butyl, sec-butyl, and iso-butyl, or R', N and R" together form a saturated heterocyclic ring of 5–7 atoms having the formula

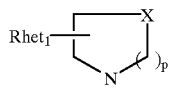

wherein p is 1, 2, or 3;

X is selected from the group consisting of $CHRhet_1$, $NRhet_1$ and O, with the proviso that p is 2 or 3 when X is $NRhet_1$ and O;

$Rhet_1$ is selected from the group consisting of hydrogen and $C_{1-5}$ alkyl, optionally functionalised with OH, F, Cl, Br, CN, $COORhet_2$, or $N(Rhet_2)_2$ wherein $Rhet_2$ independently is H or $C_{1-4}$ alkyl; or a pharmaceutically acceptable salt, hydrate or solvate thereof, to a mammal in need thereof.

2. Method according to claim 1 for stimulation, of the immune response by administering a compound of the formula (I).

3. Method according to claim 2 wherein said compound of the formula (I) is administered to a patient suffering from a cancer, wherein the disease pathology is therapeutically modified by stimulating AP-1.

4. Method according to claim 1 by administering N-[(2-diethylamino)propyl]-4-isobutyrylamino-2-methoxy-benzamide.

5. Method according to claim 1 comprising administering a compound in a daily dosage of between 0.0005 mg/kg to about 10 mg/kg body weight.

6. A compound of formula (I)

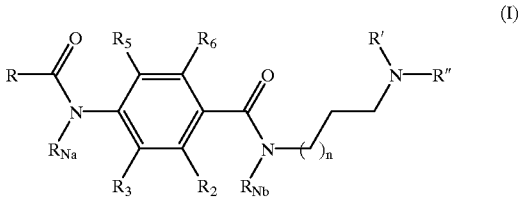

wherein

R is selected from the group consisting of methyl, ethyl, n-propyl, iso-propyl, c-propyl, n-butyl, sec-butyl, iso-butyl, tert-butyl, c-butyl, n-pentyl, sec-pentyl, iso-pentyl, tert-pentyl, neo-pentyl, c-pentyl, c-hexyl and c-heptyl;

$R_{Na}$ and $R_{Nb}$ are the same or different and selected from the group consisting of hydrogen, methyl and ethyl;

$R_2$, $R_3$, $R_5$ and $R_6$ are independently selected from the group consisting of hydrogen, methyl, methoxy, thiomethyl, hydroxy, fluoro, chloro, bromo, trifluoromethyl, phenyl and benzyl;

n is 1, 2 or 3;

R' and R" are the same or different and selected from the group consisting of methyl, ethyl, n-propyl, iso-propyl, n-butyl, sec-butyl, and iso-butyl, or R', N and R" together form a saturated heterocyclic ring of 5–7 atoms having the formula

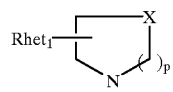

wherein p is 1, 2, or 3;

X is selected from the group consisting of $CHRhet_1$, $NRhet_1$ and O, with the proviso that p is 2 or 3 when X is $NRhet_1$ and O;

$Rhet_1$ is selected from hydrogen and $C_{1-5}$ alkyl, optionally functionalised with OH, F, Cl and Br, CN, $COORhet_2$, or $N(Rhet_2)_2$ wherein $Rhet_2$ independently is selected from H or $C_{1-4}$ alkyl;

with the proviso that when R' and R" are methyl, then R cannot be methyl; or a pharmaceutically acceptable salt, hydrate and solvate thereof.

7. Compounds according to claim 6 wherein

R is selected from methyl, ethyl, n-propyl and iso-propyl, $R_{Na}$ and $R_{Nb}$ are hydrogen, one of $R_2$, $R_3$, $R_5$ and $R_6$ is selected from methyl, methoxy, thiomethyl, hydroxy, fluoro, chloro, trifluoromethyl and phenyl, with the proviso that when R' and R" are methyl then R cannot be methyl; and R' and R" are selected from methyl, ethyl, n-propyl and n-butyl.

8. N-[(2-Diethylamino)propyl]-4-isobutyrylamino-2-methoxy-benzamide according to claim 6.

9. N-[(2-Diethylamino)propyl]-4-isobutyrylamino-2-methoxy-benzamide according to claim 7.

10. Method according to claim 2 for the treatment of rheumatoid arthritis by administering a compound of the formula (I).

11. Method according to claim 2 for the treatment of leprosy by administering a compound of the formula (I).

12. Method according to claim 2 for the treatment of HIV infection by administering a compound of the formula (I).

13. Method according to claim 1 by administering a compound in a daily dosage of between 0.005 to 1 mg/kg body weight.

14. The method according to claim 2 wherein said compound of the formula (I) is administered to a patient suffering from a cancer, wherein the cancer is responsive to immunotherapy in which the disease pathology is therapeutically modified by stimulating AP-1 in immune cells.

* * * * *

UNITED STATES PATENT AND TRADEMARK OFFICE
CERTIFICATE OF CORRECTION

PATENT NO.    : 6,518,312 B2
DATED         : February 11, 2003
INVENTOR(S)   : Anders Bjork, Gunanr Hedlund and Tomas Leanderson It is certified that error appears in the above-identified patent and that said Letters Patent is hereby corrected as shown below:

Column 5,
Lines 50-51, delete "N-[(2-Diethylamino)propyl]-4-isobutyrylamino-2-methoxy-benzamide" and insert therefor -- N-[(3-Diethylamino)propyl]-4-isobutyrylamino-2-methoxy-benzamide --

Column 6,
Line 19, delete "NaOII(aq)" and insert therefor -- Na0H(aq) --

Column 7,
Line 52, delete "N-[(2-Diethylamino)propyl[-4-isobutyrylamino-2-methoxy-benzamide" and insert therefor -- N-[(3-Diethylamino)propyl]-4-isobutyrylamino-2-methoxy-benzamide --

Column 9,
Lines 62-63, delete "N-[(2-Diethylamino)propyl]-4-isobutyrylamino-2-methoxy-benzamide" and insert therefor -- N-[(3-Diethylamino)propyl]-4-isobutyrylamino-2-methoxy-benzamide --

Column 10,
Line 61, delete"N-[(2-Diethylamino)propyl]-4-isobutyrylamino-2-methoxy-benzamide" and insert therefor -- N-[(3-Diethylamino)propyl]-4-isobutyrylamino-2-methoxy-benzamide --
Line 63, delete"N-[(2-Diethylamino)propyl]-4-isobutyrylamino-2-methoxy-benzamide" and insert therefor -- N-[(3-Diethylamino)propyl]-4-isobutyrylamino-2-methoxy-benzamide --

Signed and Sealed this

Nineteenth Day of August, 2003

JAMES E. ROGAN
*Director of the United States Patent and Trademark Office*